Sept. 1, 1953 L. C. EDWARDS Plant Pat. 1,213

PLUM TREE

Filed Oct. 26, 1951

WITNESS

Addison E. Avery

INVENTOR

Lawrence C. Edwards

Webster & Webster

ATTYS.

Patented Sept. 1, 1953

Plant Pat. 1,213

UNITED STATES PATENT OFFICE 1,213

PLUM TREE

Lawrence C. Edwards, Oakland, Calif.

Application October 26, 1951, Serial No. 253,255

1 Claim. (Cl. 47—62)

This discovery relates to a new and distinct variety of plum tree; the primary novel feature of the variety being the bearing of fruit which is deep, blackish purple in color and exceptionally large, being much larger than the Tragedy plum and ripening several days later.

Another advantageous feature of the present variety of plum tree is that the flesh of the fresh fruit—mild and delicate in flavor—is fine and melting but sufficiently firm to keep well and withstand shipping.

An additional feature of value is that the fruit of the present variety is excellent for table or dessert use; for preserving; and for drying, the fruit when dried and subsequently reconstituted being slightly tart in flavor, and the liquor is maroon color as compared with the brown liquor of the common prune.

A separate distinguishing feature of the fruit of the present variety is that it has a small, fleshy, deep, blackish purple ring about and adherent to the base of the stem, remaining on the stem when the latter is detached from ripe fruit; such fleshy ring being much more pronounced than the similar ring occasionally found in the Bradshaw plum.

Applicant, being very interested in pomology, was—by reason of such interest—led to the bringing forward of the instant variety; having accomplished the result by the following steps:

Applicant observed a small seedling initially growing by chance, recognized it as a fruit tree, dug it, and then planted it on his own premises, in Oakland, California, where it could be readily observed. Observation by applicant of this initial plant carried forward until the same grew to a mature tree; applicant recognizing, during such observation, that such tree suckered very readily.

Rather than destroying the suckers, which is recommended practice, applicant permitted them to grow for the purpose of further observation and interest with respect to their characteristics.

After applicant recognized the tendency of the original tree to sucker readily, and permitted a number of such suckers to grow to maturity rather than effect a destruction thereof, applicant was rewarded by the discovery that one of the grown-to-maturity suckers bore fruit which has novel characteristics. Such one sucker is the variety herein described and claimed, and which variety developed as a mutation of the mature tree which grew from the initial seedling.

The new and distinct variety of plum tree herein described has subsequently been successfully asexually propagated by budding onto a fruit tree root stock growing on a plot closely adjacent to applicant's premises in Oakland, California. Such reproduced fruit tree—in subsequent harvest seasons—has borne fruit, which tree and its fruit have been carefully compared with the parent tree and its fruit. As a result of such comparisons it has been ascertained that the reproduction of the variety carries forward each and every one of the novel features of the parent tree and its fruit.

Figure 1:
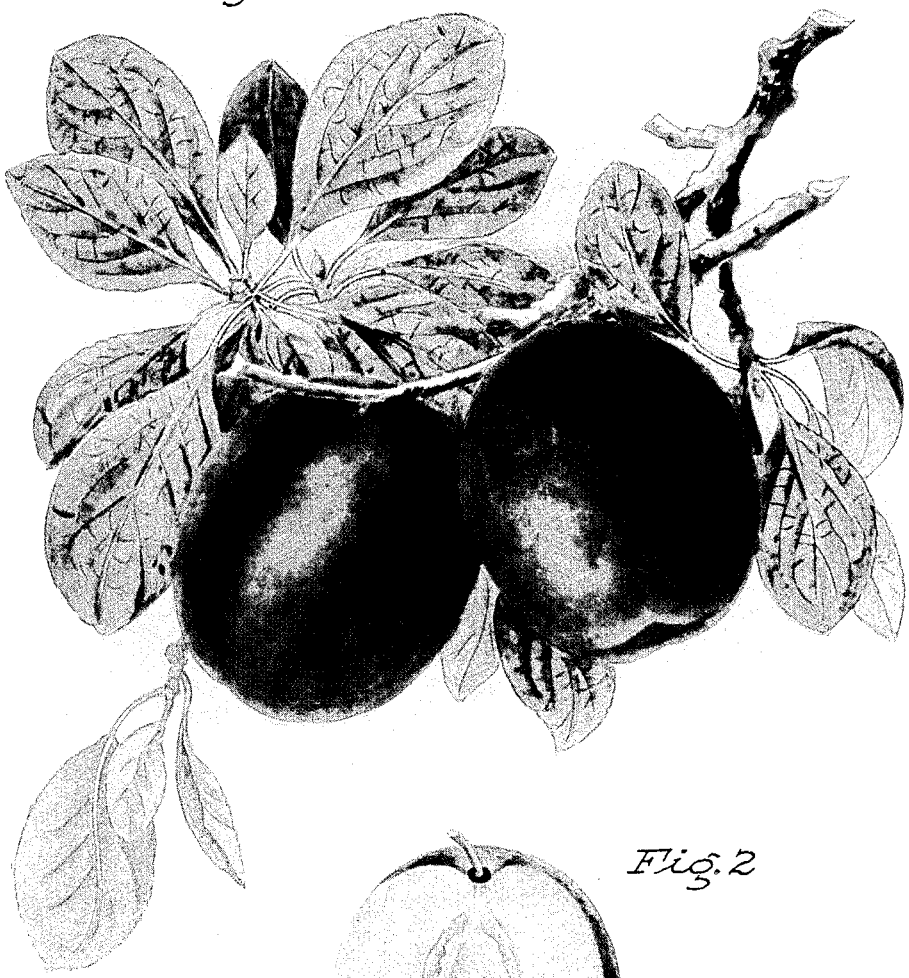
Fig. 1 is a perspective view of the fruit of the new variety, together with stems and leaves.
Figure 2:
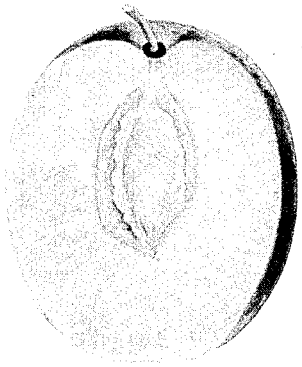
Fig. 2 is a sectional view of one of the fruit, with the stone exposed.

Referring now in more detail to the pomological characteristics of this new and distinct variety of plum tree, the following is an outline description thereof; all major color plate identifications being by reference to Maerz and Paul Dictionary of Color.

Tree: Medium size; medium vigor; upright—spreading; open; round topped; productive; regular bearer; suckers readily from the roots.

Trunk: Medium size; smooth texture.

Branches: Stocky to medium; smooth texture; gray (8–A–9) with a grayish or whitish cast; dull. Current season—shoots red.

*Lenticels.*—Numerous to medium; large size.

Leaves: Medium to small size. On spur: average length 2½″ to 3″; average width 1 to 1¼″. On shoot: average length 2″ to 3¼″; average width 1½″ to 1¾″. On spur: obovate. On shoot: round oval. Obtuse—pointed; medium thickness. Medium green (22–L–6) to darker green (23–L–6) on top side, with leaf stalks purplish red (6–H–5); lighter green (21–J–4) on under side.

*Spur.*—Smooth.

*Shoot.*—Lightly rugose.

*Margin.*—Crenate.

*Petiole.*—Medium length; medium thickness.

*Glands.*—Average number—two. Opposite; small; mixed; green; on base of blade.

*Stipules.*—Deciduous.

Flower buds: Small; medium length; conic—pointed; free; pubescent.

Flowers: Early to medium compared with other varieties. Average date first bloom—March 15th; average date full bloom—March 24th. Medium size; white.

Fruit: Very large, uniform size. Average diameter axially, 2¼″ to 2⅜″; average transversely in suture plane, 1⅞″.

*Form.*—Uniform; symmetrical; oblong; slightly compressed transversely toward suture.

*Suture.*—A relatively inconspicuous line; shallow.

*Ventral surface.*—Rounded slightly; lips nearly equal.

*Cavity.*—Rounded; elongated in suture plane with suture showing on one side. Average depth $\frac{1}{16}''$; average breadth $\frac{1}{4}''$ to $\frac{3}{8}''$.

*Markings.*—The pad, or flaring portion of the stem next to the fruit, is fleshy, forming a fleshy, slightly wrinkled ring about the stem in the cavity; such ring detaching with the stem when the fruit is ripe, and having substantially the same color as the skin of the fruit as hereinafter described.

*Base.*—Rounded.

*Stem.*—Very oblique toward suture side.

*Apex.*—Rounded to truncate, sometimes depressed.

*Pistil point.*—Apical.

Skin: Thin, tender; tenaceous to flesh—nearly free; no tendency to crack.

*Down.*—Wanting.

*Color.*—Deep, blackish purple (40–A–8), with a lighter bloom (39–A–9). (During the ripening period the fruit is initially deep red, becoming deep purplish red before reaching its maturity and final color as above.)

Flesh:

*Color.*—Light yellowish to greenish amber when firm ripe, becoming dull yellowish or brownish amber (12–L–6 to 12–L–7) when full ripe, then being semi-translucent.

*Surface of pit cavity.*—Same as flesh or with a whitish cast, full ripe fruit often lightly tinged red over part of surface of pit cavity.

*Amygdalin.*—Wanting.

*Juice.*—Moderate; rich.

*Texture.*—Medium; fine; melting.

*Fibers.*—Few; tender.

*Ripens.*—Evenly.

*Flavor.*—Subacid to mild; delicate; aroma distinct.

*Eating quality.*—Good.

Stone: Semi-free; adheres to flesh along ventral edge.

*Fibers.*—None.

*Size.*—Medium. Average length, 1 to $1\frac{1}{8}''$; average breadth, $\frac{3}{8}''$ to $\frac{7}{16}''$; average suture thickness, $\frac{5}{8}''$ to $\frac{11}{16}''$.

*Form.*—Oval.

*Base.*—Straight.

*Hilum.*—Narrow.

*Apex.*—Rounded.

*Sides.*—Equal.

*Surface.*—Lightly and finely rugose; irregularly lightly furrowed near base.

*Dorsal edge.*—Narrow, with shallow narrow groove throughout.

*Ridges.*—Continuous.

*Ventral edge.*—Narrow; sharp from base to apex; lower at base. Lateral rides, flanges, or wings wide, high, rather narrow, lower basally. Space between ventral suture and wings concave apical to middle of stone.

*Color.*—Light brown (13–G–8).

*Tendency to split.*—None.

Use: Market; dessert; culinary; shipping; drying.

Keeping quality: Good.

As compared to the other varieties of plum trees, the present variety bears deep, blackish purple fruit which is considerably larger than the Tragedy plum and ripens several days later than the same; the average ripening period of the fruit being from the third week in July to the second week in August.

The fleshly ring found about the stem base in the fruit cavity is similar to a characteristic sometimes found in the Bradshaw variety, but here is much more pronounced.

The Tragedy and Bradshaw varieties are unpatented.

The tree and its fruit herein described may vary in slight detail due to climatic and soil conditions under which the variety may be grown.

Having thus described my invention, I claim:

A new and distinct variety of plum tree substantially as described and illustrated which suckers readily from the roots and is characterized by semi-freestone fruit which is deep, blackish purple in color; exceptionally large, being much larger than the Tragedy plum, and ripening several days later; delicate in flavor; bearing a fleshy ring about and adherent to the base of the stem in the fruit cavity, such ring being the color of the skin and much more pronounced than a similar characteristic occasionally found in the Bradshaw plum; and the flesh being medium firm, fine and melting, and dull yellowish or brownish amber in color when full ripe.

LAWRENCE C. EDWARDS.

No references cited.